United States Patent [19]

Gordon

[11] 4,065,558

[45] Dec. 27, 1977

[54] SOIL TREATMENT INSECTICIDE

[75] Inventor: Fred Morris Gordon, Princeton, N.J.

[73] Assignee: American Cyanamid Company, Stamford, Conn.

[21] Appl. No.: 624,159

[22] Filed: Oct. 20, 1975

Related U.S. Application Data

[63] Continuation of Ser. No. 307,712, Nov. 17, 1972, abandoned, which is a continuation of Ser. No. 204,678, Dec. 3, 1971, abandoned.

[51] Int. Cl.² .............................................. A01N 9/36
[52] U.S. Cl. ..................................................... 424/216
[58] Field of Search ........................................ 424/216

[56] References Cited

U.S. PATENT DOCUMENTS

| | | | |
|---|---|---|---|
| 2,596,076 | 5/1952 | Hook et al. | 424/216 |
| 2,759,010 | 8/1956 | Lorenz et al. | 424/216 |
| 2,970,080 | 1/1961 | Oros et al. | 424/216 |
| 3,651,225 | 3/1972 | Gordon | 424/216 |

*Primary Examiner*—Albert T. Meyers
*Assistant Examiner*—D. W. Robinson
*Attorney, Agent, or Firm*—Robert P. Raymond

[57] ABSTRACT

This invention relates to a method for controlling the postembryonic development stages of Coleoptera and Diptera inhabiting soil by applying a toxic amount of O,O-diethyl S-(tert-butylthio)methyl phosphorodithioate to said soil in which said insects are living.

2 Claims, No Drawings

SOIL TREATMENT INSECTICIDE

CROSS REFERENCE TO RELATED APPLICATIONS

This application is a continuation-in-part of copending application Ser. No. 307,712, filed Nov. 17, 1972, now abandoned, which in turn is a continuation-in-part of application Ser. No. 204,678, filed Dec. 3, 1971 now abandoned This invention relates to a method for the control of the postembryonic development stages of Coleoptera and Diptera inhabiting the soil and the protection of agronomic crops therefrom over a prolonged period of time, characterized by applying to said soil a toxic amount of a compound selected from the group consisting of O,O-diethyl S-(ter-butylthio)methyl phosphorodithioate and O,O-diethyl S-[(1,1-dimethylpropyl)thio]methyl phosphorodithioate.

Further, this invention relates to granular pesticidal compositions of O,O-diethyl S-(tert-butylthio)methyl phosphorodithioate useful in the above methods, having an unexpectedly high level of long term pesticidal activity with a low level of phytotoxicity and being convenient to handle due to the fact that their odor is surprisingly unobjectionable. Finally, this invention relates to methods for the manufacture of said granular pesticidal compositions.

Among the agronomic crops which can be protected are: corn, sorghum, onions, peanuts, cotton, potatoes, sugar beets, rice, and other cereals.

Among the most important of the pests are the northern, southern and western corn rootworms, *Diabrotica longicornis* (Say), *Diabrotica undecimpunctata howardi* (Barber) and *Diabrotica virgifera* (Le Conte), respectively. Also of importance are the cabbage maggot, *Hylemya brassicae;* seed-corn maggot, *Hylemya cilicrura;* onion maggot, *Hylemya antiqua;* sugar beet root maggot, *Tetanoos myopaeformis;* wheat stem maggot, *Meromyza americana;* turnip maggot, *Hylemya floralis;* corn wire-worm, *Melanotus cribulosus* or *fissilis;* Oregon wireworm, *Melanotus oregonensis* (Le Conte); cotton wire-worm, *Horistonotus uhlerii,* wheat wireworm, *Agriotes mancus;* false wireworm, *Eleodes suturalis;* Columbia Basis wireworm, *Limonius subauratus* (Le Conte); western field wireworm, *Limonius infuscatus;* Pacific Coast wireworm, *Limonius canus;* sugar-beet wireworm, *Limonius californicus;* carrot rust fly larvae, *Psila rosae;* Japanese beetle larvae, *Popillia japonica;* seed-corn beetle, *Agonoderus lecontei;* Hessian fly larvae, *Mayetiola destructor;* rice water weevil, *Lissorphoptrus oryzophilus;* and June beetle larvae, *Phyllophaga rugosa,* commonly referred to as white grubs.

Heretofore, these pests were commonly controlled with chlorinated hydrocarbons. However, with continued and repeated use of such pesticides, many of the pests identified supra have developed a resistance to such chlorinated hydrocarbons, and it is now evident that the desired level of control is no longer obtainable with said compounds used at acceptable rates of application. Moreover, due to the fact that certain of the chlorinated hydrocarbons are not readily biodegradable, they have persisted in the soil for many months or even years beyond their intended useful period and have become what is believed by many to be a serious pollution problem. In light of these developments, it is apparent that it would be most advantageous if a compound could be found which (1) would afford effective control of soil-borne pests, such as described above, during the planting and growing season of the economically important crops mentioned above, and (2) would be degraded after they have served their purpose of protecting said crops from attack from the post-embryonic development stages of Diptera and Coleoptera that reside in the soil.

Inasmuch as the compounds of this invention were disclosed by Edwin O. Hook et al. in U.S. Pat. No. 2,596,076, issued May 6,. 1952 as insecticidal agents, one might be led to the conclusion that it would be obvious to anyone skilled in the art that the compounds of this invention might provide prolonged crop protection against the ravages of Coleoptera and Diptera residing in the soil. However, such assumption is believed to be erroneous, for although the patentees were concerned with a rather broad generic class of compounds and disclose insecticidal activity against a variety of insects, none of such insects were Coleoptera or Diptera which spend at least a portion of their life cycle in the soil and/or attack planted seeds or the root systems of growing crops. It is clear from the disclosure that the patentees failed to appreciate that of all the compounds disclosed only O,O-diethyl S-(tert-butylthio)methyl phosphorodithioate and O,O-diethyl S-[(1,1-dimethylpropyl)thio]methyl phosphorodithioate were unique in their class, since they exhibit extended residual activity in the soil against the post-embryonic development stages of soil inhabiting Coleoptera and Diptera.

The finding of the unique activity of the compounds of this invention is even more surprising in light of the fact that preeminent experts in the field of phosphorous insecticides, such as Dr. Gerhard Schrader and Dr. Elton Clark, teach away from the present invention by suggesting (1) that the Walter Lorenz et al. (United States Patent 2,759,010, issued August 14, 1956) compounds are tenfold to twentyfold more active as aphicides than their higher alkyl $C_4$-$C_5$ relatives (Gerhard Schrader Affidavit in File History of United States Patent 2,759,010), and (2) that the higher alkyl homologues of the structure:

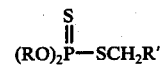

where R' is $C_3$–$C_{12}$, are less active as systemic insecticides against two-spotted spider mites than are the compounds where R' is $C_2H_5$ [Elton L. Clark et al., *Journal of Agricultural and Food Chemistry* 3(10): 834–836 (1955)].

It is surprising to find that the compounds of this invention could be applied to the soil at or about planting time and protect crops such as corn, potatoes, cotton, cole crops, onions, sorghum, peanuts, sugar beets, rice, and other cereals, from attack by the postembryonic development stages of Coleoptera and Diptera during the growing season. The compounds are particularly useful because of their extended residual effectiveness in the soil against corn rootworms, wireworms, maggots and grubs, all being economically important pests encountered in the above-named crops.

Use of the compound, O,O-diethyl S-(tert-butylthio)methyl phosphorodithioate, also has the added advantage over use of the commercial compound, O,O-diethyl S-(ethylthiomethyl) phosphorodithioate, and the above-named, O,O-diethyl S-[(1,1-dimethylpropyl)thio]methyl phosphorodithioate, in that it has an odor which is markedly less objectionable than either of said compounds. This finding is most important since the odor problems encountered in the manufacture, handling, and use of the product are substantially reduced.

In accordance with this invention, I have found that about 0.5 pound to 10 pounds per acre, of the active compound applied as a broadcast application, or from 0.3 pound to 3 pounds per acre applied in the furrow or as a band over the planted rows, provides excellent protection for the planted seeds and crops during the growing season.

Advantageously, the compounds of this invention, O,O-diethyl S-(tert-butylthio)methyl phosphorodithioate and O,O-diethyl S-[(1,1-dimethylpropyl)thio]methyl phosphorodithioate, are readily formulated for use with conventional type applicators. These compounds can be prepared as dusts, dust concentrates, emulsifiable liquids, wettable powders, and the like. Since they are liquid in their technical form, they may also be applied ultra low volume.

The granular compositions of the present invention and the method for their manufacture and the advantages thereof are described below.

Dusts may be prepared by impregnating a solid carrier with from about 1% to 25% by weight of the active material. From about 75% to 99% by weight of the inert solid carrier such as kaolin, coconut shell, corn cob grits, walnut shell, lignocellulose, attapulgite, diatomaceous earth, pumice, talc, or the like, is generally used.

Dust concentrates are made in the same fashion excepting that about 25 to 95% of the active ingredient is used. The diluent, as above-mentioned, generally constitutes the remainder of the formulation. Other additives such as sticking agents or deactivators in amounts between about 1% and 20% can be used, to avoid stability problems.

Emulsifiable concentrates can be prepared by admixing about 25 to about 95% by weight of the active material with an emulsifier, preferably an anion nonionic agent such as calcium dodecylbenzene sulfonate. Usually, about 2% to about 10% of the emulsifier is used. Where desired an inert organic solvent such as xylene or heavy aromatic naphthas such as Panasol AN-2, Esso HAN, or the like, containing about 60 to 100% aromatics and having a specific gravity between 0.88 and 1.5 at 60/60° F., may also be added.

Wettable powders are prepared in about the same manner as dust concentrates excepting that about 1 to 5% by weight of a dispersing agent such as sodium lignin sulfonate, or a monocalcium salt of a polymerized alkyl aryl sulfonic acid is admixed with the dust and generally also about 1 to 5% of a surfactant is also added such as naphthalene sulfonic acid concentrate, polyoxyethylated vegetable oil or alkyl phenoxy polyoxyethylene ethanol.

The granular pesticidal compositions of the present invention are characterized as sorptive or non-sorptive particulate granular particles having thereon between 1 and 25% by weight of a compound selected from the group consisting of O,O-diethyl S-(tert-butylthio)methyl phosphorodithioate and O,O-diethyl S-[(1,1-dimethylpropyl)thio]methyl phosphorodithioate.

These compositions have the unexpected advantages of prolonged residual activity against the postembryonic development stages of Coleoptera and Diptera inhabiting the soil. Said proloned activity provides unexpectedly effective protection of crops from the ravages of said pests.

In the case of the granulars of O,O-diethyl S-(tert-butylthio)methyl phosphorodithioate, there is a further unexpected advantage by way of removal of the unpleasant odor characterizing closely related pesticidal granulars which is of substantial advantage to the pesticide user as well as those manufacturing said granulars as described further below.

A further significant advantage for the O,O-diethyl S-(tert-butylthio)methyl phosphorodithioate granulars resides in their unexpectedly low phytotoxicity which permits the incorporation of the granular formulation in the locus of the crops, for example, by incorporating the granulars into the seed furrows at the time of planting.

As shown in comparative Examples 9-12, crops, such as peanut plants, cotton plants and sugar beets can be so protected. Corn, rice, potatoes and cole crops can be similarly protected. It will also be noted that they provide markedly superior control of root maggot infestations in alkaline soil and enhanced crop yield over the commercial granulars of O,O-diethyl S-(ethylthiomethyl) phosphorodithioate.

The granular formulations are prepared by applying about 1 to 25% by weight of O,O-diethyl S-(tert-butylthio)methyl phosphorodithioate and O,O-diethyl S-[(1,1-dimethylpropyl)thio]methyl phosphorodithioate to sorptive or non-sorptive particulate granular particles such as granular diatomites, clay, such as kaolin or attapulgite, ground corn cobs, sand, ground limestone, silica, activated carbon, and such. When non-sorptive carriers are used, the surface of the particles may be wetted with the active material and then coated with finely ground clay, talc, walnut shell flour, or other inert material. A binder or sticking agent may also be added to assure the adherence of the active material to the particles.

In the case of sorptive carriers such as clays, the clay particles are treated with a polyol deactivator such as an alkylene glycol, diethylene glycol, propylene glycol, triethylene glycol, polyethylene glycol, and the like. About 1 to 20% by weight of the deactivator is used to avoid stability problems.

In order to illustrate the present invention, the following examples are given primarily by ay of illustration. No specific details or enumerations contained therein should be construed as limitations on the present invention except insofar as they appear in the appended claims. All parts and percentages are by weight unless otherwise specifically designated.

EXAMPLE 1

Southern Corn Rootworm Control — Basic Test

Compounds are prepared as dusts on attapulgite clay or talc. The compounds are dissolved in acetone and appropriate rates obtained by serial dilution. One and one-quarter milliliters of solution is pipetted onto a standard volume of dust in one-ounce jars, and the acetone allowed to evaporate. Twenty-five milliliters of moist soil and about 200 millet seeds are placed in the jar, capped, and the contents thoroughly mixed. Ten second instar larvae of the southern corn rootworm (*Diabrotica undecimpunctata*) are then placed in each jar. Mortality counts are made after 6 days and corrected percent mortality determined. Data obtained are provided in Table I below.

From the data it can be seen that the tertiary butyl, tertiary amyl, and isopropyl homologues of compounds having the structure:

$$(C_2H_5O)_2\overset{\overset{S}{\|}}{P}-S-CH_2-S-R$$

were approximately tenfold more active than the closely related compounds included in this test. The data also suggest the criticality of the higher hommologue and the branched alkyl.

TABLE I

Percent Control of Southern Corn Rootworm Larvae from Treatment with Chemical Compounds Compound
$$(C_2H_5O)_2\overset{\overset{S}{\|}}{P}-S-CH_2-S-R$$

| R = | 10 | 1 | 0.1 |
|---|---|---|---|
| Ethyl | 100 | 100 | 0 |
| n-Propyl | 100 | 60 | 0 |
| i-Propyl | 100 | 100 | 100 |
| n-Butyl | 100 | 100 | 0 |
| i-Butyl | 100 | 100 | 0 |
| sec-Butyl | 100 | 100 | 40 |
| tert-Butyl | | | |
| tert-Butyl I | 100 | 100 | 100 |
| II | 100 | 100 | 100 |
| i-Amyl | 100 | 100 | 0 |
| tert-Amyl | 100 | 100 | 100 |
| n-Hexyl | 100 | 0 | — |
| tert-Hexyl | 100 | 60 | 0 |
| tert-Octyl | 100 | 60 | 0 |
| tert-Dodecyl | 30 | 0 | — |

EXAMPLE 2

Compound Residual Toxicity Test in Soil

Compounds are prepared as acetone solutions. Descending rates are obtained by serial dilution so that one milliliter contains the required amount of compound. One milliliter of solution is distributed over one quart of high organic prairie soil in a stainless steel beaker and then thoroughly mixed in a mechanical mixer for a uniform length of time. The treated soil is then divided between two one-pint, wide-top, paper cups. At this point, two one-ounce jars of treated soil are removed for bioassay with southern corn rootworm larvae as described in Example 1 above. The pint cups of treated soil and two one-pint cups of untreated soil are placed in a constant temperature room. One hundred milliliters of water is added to each cup of soil bringing the moisture level to near-field capacity. The soil is then allowed to dry. Water is added at approximately weekly intervals to give alternate wetting and drying throughout the test period. At biweekly intervals, one cup of soil from each treatment and untreated control is removed, thoroughly mixed, and two one-ounce jars of soil removed for bioassay with southern corn rootworm larvae.

Attached is a table giving results of initial toxicity and length of residual toxicity to southern corn rootworm larvae.

The term "prairie soil" as herein used is a Littleton silt loam having a pH of 6.7 and containing about 5.0% organic matter, 25% sand, 36% silt and 20% clay.

The data in Table II indicate a clear superiority of O,O-diethyl S-(tert-butylthio)methyl phosphorodithioate and O,O-diethyl S-[(1,1-dimethylpropyl)thio]methyl phosphorodithioate, over related compounds, for controlling southern corn rootworm in prairie soil over an extended period of time. The critical nature of the tertiary alkyl group in the molecule is evident.

It was also reported by the applicator that the O,O-diethyl S-(tert-butylthio)methyl phosphorodithioate formulation had a far less objectionable odor than any of the other formulations included in these tests.

TABLE II

Residual Control of Southern Corn Rootworm with Various Chemicals Reported as Percent Control Prairie Soil Residual Compound: $(C_2H_5O)_2P(=S)-S-CH_2-S-R$

| R = | | 1 lb./Acre Sampling Time (weeks) | | | | | | 3 lbs./Acre Sampling Time (weeks) | | | | | | 5 lbs./Acre Sampling Time (weeks) | | | | | |
|---|---|---|---|---|---|---|---|---|---|---|---|---|---|---|---|---|---|---|---|
| | | 0 | 2 | 4 | 6 | 8 | 10 | 0 | 2 | 4 | 6 | 8 | 10 | 0 | 2 | 4 | 6 | 8 | 10 |
| Ethyl | I | 100 | 30 | 0 | 0 | 0 | — | 100 | 100 | 70 | 40 | 0 | — | 100 | 100 | 100 | 100 | 100 | — |
| | II | 100 | 0 | 0 | 0 | — | — | 100 | 100 | 70 | 75 | 65 | 0 | 100 | 100 | 100 | 100 | 90 | 90 |
| n-Propyl | | 100 | 10 | 0 | 0 | — | — | 100 | 100 | 0 | 0 | — | — | 100 | 100 | 90 | 40 | — | — |
| i-Propyl | | 70 | 10 | 0 | — | — | — | 100 | 100 | 75 | 40 | — | — | 100 | 100 | 100 | 90 | 39 | — |
| n-Butyl | | 90 | 0 | 0 | — | — | — | 100 | 90 | 0 | 0 | 0 | 0 | 100 | 0 | 0 | 0 | — | — |
| i-Butyl | | 100 | 0 | 0 | 0 | 0 | 0 | 100 | 100 | 100 | 100 | 100 | 0 | 100 | 100 | 100 | 100 | 100 | 100 |
| sec-Butyl | | 100 | 100 | 30 | 40 | 0 | — | 100 | 100 | 100 | 100 | 100 | 100 | 100 | 100 | 100 | 100 | 100 | 90 |
| tert-Butyl | I | 100 | 100 | 90 | 70 | 0 | 0 | 100 | 100 | 90 | 80 | 0 | 90 | 100 | 100 | 100 | 100 | 95 | 100 |
| | II | 0 | 0 | 0 | 0 | 0 | — | 40 | 0 | 0 | 0 | 0 | — | 100 | 30 | — | — | — | — |
| i-Amyl | | 100 | 100 | 100 | 0 | 0 | — | 100 | 100 | 100 | 100 | 23 | — | 100 | 90 | 0 | 0 | 100 | — |
| tert-Amyl | | 0 | 0 | 0 | 0 | 0 | — | 60 | 70 | 0 | 0 | — | — | 0 | 0 | — | — | — | — |
| n-Hexyl | | 100 | 70 | 60 | 0 | — | — | 100 | 0 | — | — | — | — | | | | | | |
| tert-Hexyl | | 0 | 0 | 0 | — | — | — | 0 | 0 | — | — | — | — | | | | | | |

Rates lb./Acre = Broadcast equivalent
I = 1, 3 and 5 lbs./Acre (broadcast equivalent)
II = 1, 3 and 5 lbs./Acre (broadcast equivalent)

EXAMPLE 3

Southern Corn Rootworm Control

Plastic pots 7.75 inches in diameter at the top and 8 inches deep were filled to within 2.5 inches of the top with potting soil. A one-inch layer of high organic prairie soil was placed on the potting soil. A three-inch diameter circle was made in the center of the soil surface. The compound was evenly distributed on a quarter-inch diameter band around the circumference of the circle. Three field corn seeds were placed in the center of the circle and a one-inch layer of prairie soil placed on top. The pots were then removed to the greenhouse and watered. The young corn plants were thinned to one per pot. When the corn was 6 inches to 10 inches tall, the surface soil in each pot was lightly cultivated and ten third-instar southern corn rootworm larvae were placed around each plant. The extent of damage to the corn by the southern corn rootworm larvae is determined 7 days to 10 days later. Surviving corn plants were carefully removed without disturbing the treated area and three corn seeds planted. This procedure is followed at intervals until the end of the test period. At the end of each test period, the plants are examined and rated according to the rating system set forth below.

The data reported in Table III show a marked improvement in rootworm control over an extended period using the tertiary butyl and tertiary amyl compounds. These data also demonstrate that the compounds of the present invention provide protection for corn, against corn rootworm damage, for approximately 24 weeks; whereas, the ethyl compound loses its protective capacity in about 10 weeks or less. In practice, this phenomenon is of substantial importance because most varieties of field corn do not reach maturity until about 13 to 17 weeks following planting, and as such, the ethyl compound does not provide adequate protection for the maturing corn plants. Since the mature plants are tall, heavily laden, and prone to toppling when the root systems are severely damaged, protection of the root systems throughout the growing season is essential.

TABLE III

Residual Control of Southern Corn Rootworm Determined by Corn Root Damage

Structure: $(C_2H_5O)_2P(=S)-S-CH_2-S-R$

| R = | Rate/Pot | 12/23 I-II | 1/12 I-II | 2/16 I-II | 3/15 I-II | 4/12 I-II | 5/5 I-II | 6/9 I-II |
|---|---|---|---|---|---|---|---|---|
| Ethyl | 15 mg. | 0-0 | 0-0 | 0-0 | 3-0 | 3-3 | — | — |
| tert-Butyl | 15 mg. | 0-0 | 0-0 | 0-0 | 0-0 | 0-0 | 0-0 | 1-1 |
| tert-Amyl | 15 mg. | 0-0 | 0-0 | 0-0 | 0-0 | 0-0 | 0-0 | 1-1 |
| Control | No Treatment | 3-3 | 3-3 | 3-3 | 3-3 | 3-3 | 3-3 | 3-3 |

Rating System*
0 - No damage - no live rootworms
1 - Slight damage - no live rootworms
2 - Light damage - live rootworms
3 - Severe damage - live rootworms

EXAMPLE 4

Control of Western Corn Rootworm

Frozen soil naturally infested with western corn rootworm eggs was permitted to thaw at room temperature. Plastic pots 7.75 inches in diameter were filled to within 2.5 inches of the top. A 3-inch diameter circle was made in the center of the soil surface. Compounds are applied on the circumference of the circle on a quarter-inch band. About 2 inches of infested soil was placed on top. The pots were then removed to the greenhouse and watered as needed for good growing conditions. When the corn was 3 inches to 4 inches tall, it was thinned to one plant per pot. There were four replications in each treatment and seven untreated controls. Seven weeks following treatment and planting the corn plants were removed from the soil and roots examined for damage. Data obtained are reported below where damage is recorded as the number of plants having severe, moderate, slight, or no damage. From the data in Table IV, we can see that O,O-diethyl S-(tert-butylthio)methyl phosphorodithioate is markedly superior for the control of western corn rootworm when compared to the commercial compound O,O-diethyl S-(ethylthiomethyl) phosphorodithioate applied at the same rate. The applicator also reported that the odor of the latter compound was much more objectionable than its tertiary butyl homologue.

TABLE IV

Control of Western Corn Rootworm with Granular Formulations

Compound: $(C_2H_5O)_2P(=S)-S-CH_2-S-R$

| R = | Rate/Pot Active Ingredient | Severe | Moderate | Slight | None |
|---|---|---|---|---|---|
| check | | 5 | 2 | 0 | 0 |
| tert-Butyl 15G | 15 mg. | 0 | 0 | 0 | 4 |
| Ethyl 15G | 15 mg. | 0 | 0 | 1 | 3 |

15G = 15% Granular formulation

EXAMPLE 5

Southern Corn Rootworm Soil Residual Test

The compounds were prepared as 65% acetone solutions. One milliliter of solution of the required concentration was pipetted over a quart of potting soil in a stainless steel beaker approximately of 1-gallon volume. The beaker was capped and placed on a mechanical mixer for thorough mixing. The treated soil was divided between four wide-mouth, one-half pint, paper cups, moistened with 100 ml. of water, and placed in a constant temperature room. The soil is allowed to dry and then water added to give a regime of alternate wetting and drying of the soil for the duration of the test period. At intervals, the soil is removed from the cup, thoroughly mixed, and bioassayed with southern corn rootworm larvae.

Two one-ounch jars of soil was removed from each treatment, millet seed distributed throughout, and ten southern corn rootworm larvae added. After 6 days in a constant temperature room, larval counts are made and converted to corrected percent mortality.

The critical nature of the O,O-diethyl ester of the test compounds is shown by the superiority of O,O-diethyl S-(tert-butylthio)methyl phosphorodithioate over the O,O-dimethyl and O,O-diisopropyl homologues of said compounds.

20, so severe damage was done to three and sometimes four root nodes.

The method of evaluation used as as follows.

Ten roots were dug from each plot, washed to remove the soil and examined for rootworm injury. Room condition was rated according to the following categories of damage:

0 = No apparent damage
1 = Some feeding injury but no severe pruning
2 = Some root pruning but less than one node equivalent pruned or severely injured
3 = At least one node less than two nodes severely pruned
4 = Two to three nodes pruned
5 = Three or more nodes pruned

TABLE V
Southern Corn Rootworm Control

| Compound | Rate per quart Soil | % Corrected Mortality Southern Corn Rootworm Weeks After Treatment | | | | |
|---|---|---|---|---|---|---|
| | | 0 | 1 | 2 | 3 | 6 |
| $(CH_3O)_2P(S)-S-CH_2-S-C(CH_3)_3$ | 10 mg. | 100 | 100 | 84 | 0 | — |
| | 6 mg. | 100 | 33 | — | — | — |
| | 3 mg. | 84 | 0 | — | — | — |
| $[(CH_3)_2CHO]_2P(S)-S-CH_2-S-C(CH_3)_3$ | 10 mg. | 100 | 83 | 79 | 0 | — |
| | 6 mg. | 100 | 0 | — | — | — |
| | 3 mg. | 95 | 0 | — | — | — |
| $(C_2H_5O)_2P(S)-S-CH_2-S-C(CH_3)_3$ | 6 mg. | 100 | 100 | 100 | 100 | 100 |
| | 3 mg. | 100 | 100 | 100 | 100 | 100 |
| | 1 mg. | 100 | 100 | 100 | 90 | 70 |

EXAMPLE 6

Western Corn Rootworm Control — Field Tests

Row treatments with granules were applied through a seven-inch bander mounted on the planter ahead of the press wheel.

Furrow treatments were applied by removing the bander and allowing the granules to flow from the delivery tube directly into the seed furrow.

Two rows, 50 feet long, were used for each treatment, and twice replicated in each field.

The plots were located on silt loam soil with a pH of about 6.6, 20% clay and about 3% organic matter. Phosphate and potash levels were adequate but 100 pounds of nitrogen was added during seed bed preparation.

Spring tillage consisted of plowing, disking and harrowing prior to planting. Weeds were controlled with a preemergence application of Ramrod-Atrazin (a herbicidal composition). Plots were cultivated once.

Two different varieties of field corn (1) Kt 657 and (2) Pioneer 3306 were used in these tests.

Worms were first found on corn roots on June 10. A peak population of 40 to 50 worms per plant occurred about the first week of July. An average of ten or more worms per plant was present from about June 20 to July Previous years correlation studies indicated the plants with ratings of 3 or higher were subject to lodging and yield reduction. Thus, the tabulation of "Roots rating 3 or worse" should indicate the practical acceptability of a treatment. Actual lodging and yield data will be collected later in the season.

Root damage ratings were made during the last two weeks of July.

In order to detect small differences between good treatments, the number of damaged rootlets on each root was also recorded. An average of 40 rootlets on three nodes was used for these calculations.

Stand counts of corn are shown in Tables VI and VII. Tables VIII, IX, X and XI show the root damage evaluations from the two plots.

The marked superiority of O,O-diethyl S-(tert-butylthio)methyl phosphorodithioate over O,O-diethyl S-(ethylthiomethyl) phosphorodithioate, when used in the field for controlling western corn rootworm, is shown by the data in Tables VI through XI. The applicator also reported a noticeable and much less objectionable odor eminating from the O,O-diethyl S-(tert-butylthio)methyl phosphorodiethioate formulation than from the O,O-diethyl S-(ethylthiomethyl) phosphorodithioate formulation.

TABLE VI

Stand Counts (Kt 657 - Field Corn) - Western Corn Rootworm Control

| Compound | Treatment | Dosage lb./Acre | Method of Application | Corn Plants/40 ft. of Row I | II | Average |
|---|---|---|---|---|---|---|
| $(C_2H_5O)_2\overset{S}{\overset{\|}{P}}-S-CH_2-S-\overset{CH_3}{\overset{\|}{\underset{\|}{C}}}-CH_3$ $\phantom{xxxxxxxxxxxx}CH_3$ | 2.5% G | 0.25 | band | 40 | 40 | 40 |
| | 2.5% G | 0.25 | furrow | 41 | 39 | 40 |
| | 5% G | 0.5 | band | 43 | 41 | 42 |
| | 5% G | 0.5 | furrow | 40 | 38 | 39 |
| | 10% G | 1.0 | band | 42 | 41 | 41.5 |
| | 10% G | 1.0 | furrow | 41 | 42 | 41.5 |
| $(C_2H_5O)_2\overset{S}{\overset{\|}{P}}-S-CH_2-S-C_2H_5$ | 2.5% G | 0.25 | band | 40 | 42 | 41 |
| | 2.5% G | 0.25 | furrow | 42 | 41 | 41.5 |
| | 5% G | 0.5 | band | 42 | 41 | 41.5 |
| | 5% G | 0.5 | furrow | 41 | 40 | 41.5 |
| | 10% G | 1.0 | band | 41 | 39 | 40 |
| | 10% G | 1.0 | furrow | 40 | 40 | 40 |
| | 15% G | 1.0 | band | 41 | 40 | 40.5 |
| Control | — | — | — | 39 | 42 | 40.5 |

G = Granules

TABLE VII

Stand Counts (Pioneer 3306 - Field Corn) - Western Corn Rootworm Control

| Compound | Treatment | Dosage lb./Acre | Method of Application | Corn Plants/40 ft. of Row I | II | Average |
|---|---|---|---|---|---|---|
| $(C_2H_5O)_2\overset{S}{\overset{\|}{P}}-S-CH_2-S-\overset{CH_3}{\overset{\|}{\underset{\|}{C}}}-CH_3$ $\phantom{xxxxxxxxxxxx}CH_3$ | 2.5% G | 0.25 | band | 45 | 43 | 44 |
| | 2.5% G | 0.25 | furrow | 45 | 40 | 43 |
| | 5% G | 0.5 | band | 43 | 43 | 43 |
| | 5% | 0.5 | furrow | 43 | 44 | 44 |
| | 10% G | 1.0 | band | 45 | 43 | 44 |
| | 10% G | 1.0 | furrow | 43 | 46 | 45 |
| $(C_2H_5O)_2\overset{S}{\overset{\|}{P}}-S-CH_2-S-C_2H_5$ | 2.5% G | 0.25 | band | 45 | 42 | 44 |
| | 2.5% G | 0.25 | furrow | 45 | 41 | 43 |
| | 5% G | 0.5 | band | 44 | 44 | 44 |
| | 5% G | 0.5 | furrow | 45 | 45 | 45 |
| | 10% G | 1.0 | band | 44 | 44 | 44 |
| | 10% G | 1.0 | furrow | 43 | 43 | 43 |
| | 15% G | 1.0 | band | 44 | 45 | 45 |
| Control | — | — | — | 45 | 44 | 45 |

G = Granules

TABLE VIII

Root Damage Ratings (Kt 657 - Field Corn) - Western Corn Rootworm Control

| Compound | Treatment | Dosage lb./Acre | Method of Application | Average Root Rating I | II | No. 3 Rated Roots/20 Roots |
|---|---|---|---|---|---|---|
| $(C_2H_5O)_2\overset{S}{\overset{\|}{P}}-S-CH_2-S-\overset{CH_3}{\overset{\|}{\underset{\|}{C}}}-CH_3$ $\phantom{xxxxxxxxxxxx}CH_3$ | 2.5% G | 0.25 | band | 2.4 | 2.1 | 4 |
| | 2.5% G | 0.25 | furrow | 2.0 | 2.1 | 3 |
| | 5% G | 0.5 | band | 1.8 | 1.9 | 1 |
| | 5% G | 0.5 | furrow | 1.8 | 2.7 | 4 |
| | 10% G | 1.0 | band | 1.2 | 1.2 | 0 |
| | 10% G | 1.0 | furrow | 1.2 | 1.4 | 0 |
| $(C_2H_5O)_2\overset{S}{\overset{\|}{P}}-S-CH_2-S-C_2H_5$ | 2.5% G | 0.25 | band | 3.3 | 2.4 | 12 |
| | 2.5% G | 0.25 | furrow | 2.8 | 2.9 | 11 |
| | 5% G | 0.5 | band | 1.9 | 2.7 | 7 |
| | 5% G | 0.5 | furrow | 2.0 | 2.9 | 9 |
| | 10% G | 1.0 | band | 1.4 | 1.4 | 1 |
| | 10% G | 1.0 | furrow | 1.2 | 1.8 | 0 |
| | 15% G | 1.0 | band | 1.4 | 2.2 | 3 |
| Control | — | — | — | 4.1 | 4.2 | 20 |

G = Granules

TABLE IX

Damaged Rootlet Counts (Kt 657 - Field Corn) - Western Corn Rootworm Control

| Compound | Treatment | Dosage lb./Acre | Method of Application | Damaged Rootlets/Plant[1] I | II | Average |
|---|---|---|---|---|---|---|
| $(C_2H_5O)_2\overset{S}{\overset{\|}{P}}-S-CH_2-S-\overset{CH_3}{\overset{\|}{\underset{\|}{C}}}-CH_3$ $\phantom{xxxxxxxxxxxx}CH_3$ | 2.5% G | 0.25 | band | 9.0 | 11.8 | 10.4 |
| | 2.5% G | 0.25 | furrow | 5.5 | 9.3 | 7.4 |
| | 5% G | 0.5 | band | 4.2 | 7.8 | 6.0 |
| | 5% G | 0.5 | furrow | 4.6 | 12.0 | 8.3 |
| | 10% G | 1.0 | band | 2.8 | 2.4 | 2.6 |
| | 10% G | 1.0 | furrow | 3.3 | 2.0 | 2.7 |
| $(C_2H_5O)_2\overset{S}{\overset{\|}{P}}-S-CH_2-S-C_2H_5$ | 2.5% G | 0.25 | band | 18.0 | 13.6 | 15.8 |
| | 2.5% G | 0.25 | furrow | 11.5 | 15.0 | 13.3 |
| | 5% G | 0.5 | band | 5.5 | 14.6 | 10.1 |
| | 5% G | 0.5 | furrow | 6.2 | 16.5 | 11.4 |
| | 10% G | 1.0 | band | 2.7 | 5.0 | 3.9 |
| | 10% G | 1.0 | furrow | 4.5 | 8.1 | 6.3 |
| | 15% G | 1.0 | band | 5.0 | 9.4 | 7.2 |

TABLE IX-continued

Damaged Rootlet Counts (Kt 657 - Field Corn) - Western Corn Rootworm Control

| Compound | Treatment | Dosage lb./Acre | Method of Application | Damaged Rootlets/Plant[1] I | II | Average |
|---|---|---|---|---|---|---|
| Control | — | — | — | 28.0 | 30.0 | 29.0 |

[1]Average of 10 plants
G = Granules

TABLE X

Root Damage Ratings (Pioneer 3306 - Field Corn) - Western Corn Rootworm Control

| Compound | Treatment | Dosage lb./Acre | Method of Application | Average Root Rating I | II | No. 3 Rated Roots/20 Roots |
|---|---|---|---|---|---|---|
| $(C_2H_5O)_2\overset{\overset{S}{\|\|}}{P}-S-CH_2-S-\underset{\underset{CH_3}{\|}}{\overset{\overset{CH_3}{\|}}{C}}-CH_3$ | 2.5% G | 0.25 | band | 4.0 | 2.4 | 14 |
| | 2.5% G | 0.25 | furrow | 2.8 | 2.9 | 17 |
| | 5% G | 0.5 | band | 2.6 | 2.3 | 9 |
| | 5% G | 0.5 | furrow | 2.6 | 2.6 | 11 |
| | 10% G | 1.0 | band | 2.3 | 1.7 | 3 |
| | 10% G | 1.0 | furrow | 1.9 | 2.2 | 3 |
| $(C_2H_5O)_2\overset{\overset{S}{\|\|}}{P}-S-CH_2-S-C_2H_5$ | 2.5% | 0.25 | band | 4.1 | 4.7 | 20 |
| | 2.5% G | 0.25 | furrow | 2.9 | 3.3 | 19 |
| | 5% G | 0.5 | band | 3.4 | 3.8 | 20 |
| | 5% G | 0.5 | furrow | 3.3 | 3.8 | 19 |
| | 10% G | 1.0 | band | 1.7 | 2.3 | 3 |
| | 10% G | 1.0 | furrow | 1.8 | 1.9 | 0 |
| | 15% G | 1.0 | band | 3.2 | 2.6 | 15 |
| Control | — | — | — | 4.9 | 4.9 | 20 |

TABLE XI

Damaged Rootlet Count - Scamehorn Plot - Western Corn Rootworm Control

| Compound | Treatment | Dosage lb./Acre | Method of Application | Damaged Rootlets/Plant[1] I | II | Average |
|---|---|---|---|---|---|---|
| $(C_2H_5O)_2\overset{\overset{S}{\|\|}}{P}-S-CH_2-S-\underset{\underset{CH_3}{\|}}{\overset{\overset{CH_3}{\|}}{C}}-CH_3$ | 2.5% G | 0.25 | band | 30.0 | 10.5 | 21.0 |
| | 2.5% G | 0.25 | furrow | 18.0 | 15.5 | 17.0 |
| | 5% G | 0.5 | band | 15.0 | 8.0 | 11.5 |
| | 5% G | 0.5 | furrow | 16.0 | 9.0 | 12.5 |
| | 10% G | 1.0 | band | 14.5 | 5.0 | 10.0 |
| | 10% G | 1.0 | furrow | 14.3 | 9.7 | 12.0 |
| $(C_2H_5O)_2\overset{\overset{S}{\|\|}}{P}-S-CH_2-S-C_2H_5$ | 2.5% G | 0.25 | band | 31.0 | 37.0 | 34.0 |
| | 2.5% G | 0.25 | furrow | 16.0 | 21.0 | 19.0 |
| | 5% G | 0.5 | band | 24.0 | 28.0 | 26.0 |
| | 5% G | 0.5 | furrow | 23.0 | 28.0 | 26.0 |
| | 10% G | 1.0 | band | 11.3 | 8.5 | 10.0 |
| | 10% G | 1.0 | furrow | 12.1 | 4.5 | 8.3 |
| | 15% G | 1.0 | band | 22.0 | 13.0 | 18.0 |
| Control | — | — | — | 39.0 | 39.0 | 39.0 |

[1]Average of 10 plants

EXAMPLE 7

Control of the postembryonic development stages of Diptera residing in the soil is demonstrated in the following test wherein Downing yellow globe onion seed, treated with tetramethylthiuram disulphide (a commercial fungicide), is planted in four 10 foot rows at two separate locations. A 15% granular formulation of O,O-diethyl S-(tert-butylthio)methyl phosphorodithioate is applied in the furrow at planting at the rate of 7 pounds per acre, which is equivalent to one pound per acre of technical material. Untreated seeds and seeds treated with tetramethylthiuram disulphide or N-trichloromethylmercapto-4-cyclohexene-1,2-dicarboximide (another commercial fungicide), are planted at the same time and in the same manner as described above for use as controls. Nine weeks after planting all plants are examined for onion maggot damage and rated as follows:

Ratings
1 = even stand
2 = uneven — slight damage
3 = uneven — moderate damage
4 = uneven — severe damage
5 = complete destruction

TABLE XII

Onion Maggot Test

| Formulation | Rate lbs./Acre Actual | Ratings Site 1 | Site 2 |
|---|---|---|---|
| O,O-diethyl S-(tert-butylthio)methyl phosphorodithioate | 1.05 | 1.0 | 1.3 |
| Untreated (A) | — | 5.0 | 3.3 |
| Untreated (C) | — | 5.0 | 4.8 |
| Untreated | — | 5.0 | 4.5 |
| Untreated | — | 5.0 | 4.0 |

(A) = Seed treated with tetramethylthiuram disulphide.
(C) = Seed treated with N-trichloromethylmercapto-4-cyclohexene-1,2-dicarboximide.

EXAMPLE 8

Granules of

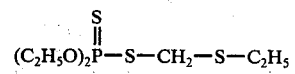

(10% granules) and

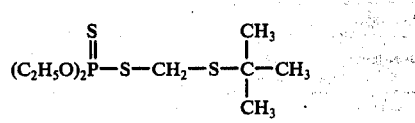

(15% granules) were applied in the seed furrow at the rate of 1.0 lb. per acre of active ingredient with the sugar beet seed at the time of planting in order to determine the effectiveness of said compounds for controlling sugar beet root maggot (*Tetanops myopaeformis*). One hundred days later, sugar beets were dug and maggots counted. There was no phytotoxicity by either compound to the emerging seedlings. The following table shows the superiority of

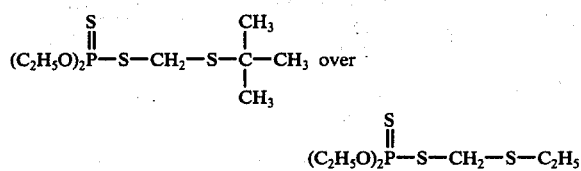

for the control of this dipterous larvae.

TABLE XIII

| Insecticide | Average Number Maggots/ Beet | % Maggot Reduction |
|---|---|---|
| (C₂H₅O)₂P(S)—S—CH₂—S—C₂H₅  10G | 18.7 | 70.0 |
| (C₂H₅O)₂P(S)—S—CH₂—S—C(CH₃)₃  15G | 13.2 | 78.7 |
| Untreated | 62.4 | — |

10G = 10% Granules
15G = 15% Granules

EXAMPLE 9

In the following tests, O,O-diethyl S-(tert-butylthio)methyl phosphorodithioate and O,O-diethyl S-(ethylthiomethyl) phosphorodithioate are compared for efficacy in controlling thrips on peanuts. A determination of phytotoxicity of said compounds on peanut plants is also made.

The compounds are applied as granular formulations in the seed furrows at the time of planting. Applications are made at the 1 pound per acre rate for each compound with four (4 rows - 36 inch centers × 50 feet long) plots per treatment randomized in each tier of replicates. Four months after planting and treatment, all plots are examined and rated for thrip damage and phytotoxicity. Data obtained are reported below.

TABLE XIV
Thrip Control and Phytotoxicity on Peanut Plants

| Insecticide | Rate lb./Acre | Replicate Number | Phytotoxicity[a] (0–5) 6/2/71 | Thrips Damage[b] (0–10) 6/2/71 |
|---|---|---|---|---|
| (C₂H₅O)₂P(S)—S—CH₂—S—C(CH₃)₃ | 1.0 | 1 | 1.0 | 0.0 |
| | | 2 | 0.0 | 1.0 |
| | | 3 | 0.0 | 0.0 |
| | | 4 | 1.0 | 0.0 |
| | | Average | 0.5 | 0.25 |
| (C₂H₅O)₂P(S)—S—CH₂—S—C₂H₅ | 1.0 | 1 | 2.0 | 0.0 |
| | | 2 | 3.0 | 0.0 |
| | | 3 | 2.0 | 1.0 |
| | | 4 | 2.0 | 0.0 |
| | | Average | 2.25 | 0.25 |
| None | — | 1 | 0.0 | 9.0 |
| | | 2 | 0.0 | 8.0 |
| | | 3 | 0.0 | 9.0 |
| | | 4 | 0.0 | 7.0 |
| | | Average | 0.0 | 8.25 |

[a] 0 = no phytotoxicity, 5 = extreme phytotoxicity with stand reduction, 3 and 4 = leaf burn.
[b] 0 = no thrips damage, 10 = severe thrips damage with stand reduction.

EXAMPLE 10

The following tests were conducted to (1) determine the effectiveness of O,O-diethyl S-(tert-butylthio)methyl phosphorodithioate for controlling thrips on cotton plants, and (2) ascertain whether said compound is phytotoxic to said plants at effective insecticidal rates of application.

In these tests, O,O-diethyl S-(tert-butylthio)methyl phosphorodithioate and O,O-diethyl S-(ethylthiomethyl) phosphorodithioate were applied as granular formulations in the seed furrow at the time of planting. Rates of application were from 0.5 pound to 1.0 pound per acre of active compound, and untreated rows were employed as controls. Four months after planting all plots were examined for (1) phytotoxic effects, (2) plant vigor, (3) stand, and (4) thrip control.

Data obtained are reported below where it can be seen that both insecticides provided excellent thrip cntrol. However, plants treated with O,O-diethyl S-(ethylthiomethyl) phosphorodithioate were injured as evidenced by stand reduction and positive phytotoxicity and vigor ratings.

TABLE XV
Determination of Thrip Control and Phytotoxicity on Cotton Plants

| Insecticide | Rate lb./Acre | Phytotoxicity[a] (1–4) | Vigor[b] (1–4) | Stand (plants per 10 feet of row) | Thrip Control[c] (1–4) |
|---|---|---|---|---|---|
| (C₂H₅O)₂P(S)—S—CH₂—S—C(CH₃)₃ | 1.0 | 1 | 1 | 69 | 1 |
| | 0.5 | 1 | 1 | 60 | 1.3 |

TABLE XV-continued

Determination of Thrip Control and Phytotoxicity on Cotton Plants

| Insecticide | Rate lb./Acre | Phyto-toxicity[a] (1–4) | Vigor[b] (1–4) | Stand (plants per 10 feet of row) | Thrip Control[c] (1–4) |
|---|---|---|---|---|---|
| $\overset{S}{\underset{\parallel}{(C_2H_5O)_2P}}-S-CH_2-S-C_2H_5$ | 0.75 | 1.3 | 1.3 | 36 | 1 |
| Control 1 | — | 1 | 2 | 50 | 4 |
| Control 2 | — | 1 | 2 | 47 | 3.6 |
| Control 3 | — | 1 | 1.3 | 40 | 4 |
| Control 4 | — | 1 | 1.3 | 46 | 4 |

[a]1 = No injury, 4 = severe injury.
[b]1 = Excellent vigor, 4 = plants growing very poorly.
[c]1 = Excellent control, 4 = no control.

EXAMPLE 11

Insect Control in Sugar Beets

Protection of sugar beets from attack by the beet leaf miner (*Pegomya betae*) and the root feeder (*Bothinoderis sp.*) is demonstrated by the following tests, wherein 10% granular formulations of O,O-diethyl S-(tert-butylthio)methyl phosphorodithioate and O,O-diethyl S-(ethylthiomethyl) phosphorodithioate were applied to the soil at planting time. Applications were made so as to provide from 20 kg. to 30 kg. per nectar of active compound. Test plots were 50 square meters, and each treatment was replicated six times.

Three months after treatment all plants were examined to determine the numer of root attacks made per 1000 plants, the percent leaf damage occurring, and the percent control achieved. Data obtained are reported below.

spaced at 7 per foot of row. The rows were fertilized twice during the growing season. Seedling stands were evaluated by counting the number of beet-containing inches in four 100-inch lengths of row. Stand and yield at harvest were estimated by counting and weighing beets on 50-foot lengths of the two control rows. Root maggot infestations were estimated on each plot late in August by counting the maggots in ten soil samples, each 8 inches square and 14 inches deep. Each sample was centered on a beet in the outside row.

The soil in which these tests were conducted was a sandy loam, pH 7.4; organic matter, 7.6%; conductivity, 0.52%; $CaCO_3$ equivalent, 1.08%.

From the data obtained and reported below, it can be seen that in alkaline soil O,O-diethyl S-(tert-butylthio)-methyl phosphorodithioate provides better maggot control and markedly better crop yield than O,O-diethyl S-(ethylthiomethyl) phosphorodithioate.

TABLE XVII

Improved Maggot Control and Crop Yield in Treated Sugar Beets

| Insecticide | Rate lb./Acre | Maggots Per Beet | % Control | Harvested Beets Number Per Row | Harvested Beets Tons/Acre |
|---|---|---|---|---|---|
| None | 0 | 62.4 | — | 79 | 10.9 |
| $\overset{S}{\underset{\parallel}{(C_2H_5O)_2P}}-S-CH_2-S-C_2H_5$ | 1.0 | 18.7 | 70 | 88 | 12.8 |
| $\overset{S}{\underset{\parallel}{(C_2H_5O)_2P}}-S-CH_2-S-C(CH_3)_3$ | 1.0 | 13.2 | 79 | 83 | 13.5 |

TABLE XVI

Insect Control in Sugar Beets

| Insecticide | Rate lb./Acre | Number Root Attacks (1000 Plants) | % Control | % Leaf Area Damage |
|---|---|---|---|---|
| None | 0.0 | 838.7 | — | 26.2 |
| $\overset{S}{\underset{\parallel}{(C_2H_5O)_2P}}-S-CH_2-S-C_2H_5$ | 25.0 | 178.5 | 78.8 | 7.7 |
| $\overset{S}{\underset{\parallel}{(C_2H_5O)_2P}}-S-CH_2-S-C(CH_3)_3$ | 20.0 | 91.7 | 89.1 | 5.7 |
|  | 30.0 | 58.0 | 93.1 | 3.7 |

EXAMPLE 12

Insect Control and Improved Yield of Sugar Beets in Alkaline Soil

In these tests, compounds were applied to the seed furrow as granular formulations at the rate of one pound per acre active compound. Plots consisted of 4 rows 60 feet long and each treatment was replicated six times, in randomized block design. Monogerm seed was planted in mid-May in furrows at a depth of ¾ inch and

EXAMPLE 13

Comparative Toxicity of O,O-Diethyl S-(tert-butylthio)methyl phosphorodithioate and O,O-Diethyl S-(ethylthio)methyl phosphorodithioate Soil Insecticide to False Wireworm Larvae, *Eleodes suturalis* (Say).

O,O-Diethyl S-(tert-butylthio)methyl phosphorodithioate and O,O-diethyl S-(ethylthio)methyl phosphorodithioate were prepared in 65% acetone/35% water solutions so that 1 ml of solution delivers 6 mg, 3 mg and 1 mg of active ingredient per quart of potting soil (equivalent to 6, 3 and 1 lb/acre broadcast or 1, 0.5 and 0.17 lb/acre on a 7-inch band with 42-inch row spacing). One quart of moist (about 25% of moisture holding capacity) potting soil was placed in a stainless steel beaker approximately 22 cm deep × 18 cm diameter. One milliliter of solution was distributed dropwise over the soil. The beaker was then capped and rotated on a mechanical mixer for 2 minutes (60 revolutions). Two 1-ounce jars of soil were removed and 3 wheat seeds mixed in the soil as food for the false wireworm larvae (about 5 mm long) placed in the jar. The infested treated jars of soil and the infested untreated check were held in the holding room at 84° F and 44% r.h. for 6 days when mortality counts were made.

TABLE XVIII

Control of False Wireworm Larvae

| Treatment | Rate ai per qt. Soil | % Mortality |
|---|---|---|
| O,O-Diethyl S-(ethylthio)methyl phosphorodithioate | 6 mg | 0 |
|  | 3 mg | 0 |
|  | 1 mg | 0 |
| O,O-Diethyl S-(tert-butylthio)-methyl phosphorodithioate | 6 mg | 100 |
|  | 3 mg | 20 |
|  | 1 mg | 20 |
| Check | — | 0 |

EXAMPLE 14

Control of Carrot Rust Fly, Psila rosae (Fabricius) with O,O-Diethyl S-(tert-butylthio)methyl phosphorodithioate.

to determine the effectiveness of O,O-diethyl S-(tert-butylthio)methyl phosphorodithioate for controlling the carrot rust fly larvae, 10% granular formulations of O,O-diethyl S-(tert-butylthio)methyl phosphorodithioate and O,O-diethyl S-(ethylthio)methyl phosphorodithioate were prepared and evaluated in a field test with carrots in sandy loam soil. Each of the above-named compounds were applied at the rate of 1.5 lb. active ingredient per acre (1.68 kg/ha) at planting time in a 6-inch (15.2 cm) band using the "bow wave" method of application. In another treatment, 1.5 lb. per acre of each of the above-named compounds were applied in similar manner; however, 1.0 lb. ai per acre (1.12 kg/ha) of compound was applied as a supplemental treatment 99 days later. The supplement treatment was applied over the foliage and lightly raked into the soil.

Plots were two single rows 25 feet (7.5 m) long and 15 inches (38.3 cm) wide arranged in randomized block design and replicated five times. Treatments were made April 20 and July 28; carrots were harvested, examined and rated on November 22.

Evaluation was based on the percentage of carrots damaged. O,O-Diethyl S-(tert-butylthio)methyl phosphorodithioate gave significantly better control of the carrot rust fly by both treatments referred to above, than O,O-diethyl S-(ethylthio)methyl phosphorodithioate. Data obtained are reported in Table XIX below.

TABLE XIX

Carrot Rust Fly Control

| Compound | Rate (lb. ai/acre) At Planting | Rate (lb. ai/acre) Supplementary | Carrot Fly Damage % Attacked | Carrot Fly Damage % Reduction from Control |
|---|---|---|---|---|
| O,O-Diethyl S-(ethylthio)methyl phosphorodithioate | 1.5 | — | 53 | 56.0 |
|  | 1.5 | 1.0 | 17 | 89.2 |
| O,O-Diethyl S-(tert-butylthio)-methyl phosphorodithioate | 1.5 | — | 17 | 89.2 |
|  | 1.5 | 1.0 | 6 | 96.7 |
| Control | — | — | 65.9 | — |

EXAMPLE 15

Control of Northern Corn Rootworm, Diabrotica longicornis (Say) with O,O-Diethyl S-(tert-butyltho)methyl phosphorodithioate.

In the following test, O,O-diethyl S-(tert-butylthio)methyl phosphorodithioate and O,O-diethyl S-(ethylthio)methyl phosphorodithioate were prepared as 15% granular formulations and applied as a 7-inch (17.8 cm) band over the row at 1 lb. actual per acre (1.12 kg/ha), based on a 40-inch (101.6 cm) row.

Pride 121 variety field corn was planted on 40-inch (101.6 cm) centers on May 23. Plots were made up of rows 350 feet (105 m) long and treated with test compounds as described.

Evaluations were made on August 22, by digging, washing and rating root damage to 30 plants randomly selected from each treatment. The rating system utilized was the Iowa State University System which ranges from 1, no damage, to 6, severe damage, and pruning to three root nodes.

The data reveal that a heavier infestation of northern corn rootworms was controlled with O,O-diethyl S-(tert-butylthio)methyl phosphorodithioate and that this control was superior to that obtained with O,O-diethyl S-(ethylthio)methyl phosphorodithioate. Data are reported in Table XX below.

TABLE XX

Northern Corn Rootworm Control

| Compound | Rate (kg/ha) based on 101.6 cm row | Root Damage Rating |
|---|---|---|
| O,O-Diethyl S-(tert-butylthio)-methyl phosphorodithioate | 1.12 | 2.37 |
| O,O-Diethyl S-(ethylthio)methyl phosphorodithioate | 1.12 | 2.70 |
| Control | — | 4.90 |

EXAMPLE 16

Control of Wireworms, Melantous fissilis and Hemicrepidus spp. with O,O-Diethyl S-(tert-butylthio)methyl phosphorodithioate.

O,O-Diethyl S-(tert-butylthio)methyl phosphorodithioate and O,O-diethyl S-(ethylthio)methyl phosphorodithioate were prepared as 15% granular formulations and evaluted for the control of wireworms, including the corn wireworm, infesting Irish potatoes.

Each of the above formulations were applied at 3.0 lbs. ai/acre (3.36 kg/ha) in 28-inch (71.12 cm) rows.

Plots, on well drained loam soil, consisted of two-row treatments 60 feet (18 m) long replicated four times. Russet Burbank potatoes were treated by applying the formulated compounds in the furrow as bands on either side of the seed piece at planting. Evaluations were made by determining the percentage of tubers injured by wireworms. Results are given in Table XXI below.

TABLE XXI

Wireworm Control

| Compound | Rate kg ai/ha | Average % Tubers Damaged |
| --- | --- | --- |
| O,O-Diethyl S-(tert-butylthio)methyl phosphorodithioate | 3.36 | 0.7 |
| O,O-Diethyl S-(ethylthio)methyl phosphorodithioate | 3.36 | 1.7 |
| Control | — | 2.9 |

EXAMPLE 17

Control of Wireworms, *Melanotus Communis*, with O,O-Diethyl S-(tert-butylthio)methyl phosphorodithioate.

The control of wireworms in corn with O,O-diethyl S-(tert-butylthio)methyl phosphorodithioate was evaluated in the following tests, wherein 15% granular formulations of O,O-diethyl S-(tert-butylthio)methyl phosphorodithioate and O,O-diethyl S-(ethylthio)methyl phosphorodithioate were applied at planting time in a 6-inch (15.24 cm) band over the open furrow to provide 1.0 lb. per acre active ingredient (1.12 kg/ha). Pioneer 3368 variety field corn was planted April 25, in loam soil in rows with 38-inch (0.95 m) centers. Test plots were four rows by 35 feet (10.5 m) replicated four times. An untreated check was included, and the plots were established in a randomized complete block design. Wireworm infestation was heavy.

Evaluation of the compounds was by counting the number of wireworm damaged plants per 116 feet of row per replicate. The average mean damage and calculated number of damaged plants per acre demonstrate that O,O-diethyl S-(tert-butylthio)methyl phosphorodithioate is superior to O,O-diethyl S-(ethylthio)methyl phosphorodithioate for controlling wireworms. Data are reported in Table XXII below.

TABLE XXII

Wireworm Control

| Compound | Rate kg/ha | Mean Number of Damaged Plants per Plot | Damaged Plants per Hectare |
| --- | --- | --- | --- |
| O,O-Diethyl S-(tert-butylthio)methyl phosphorodithioate | 1.12 | 11.8 | 3,468 |
| O,O-Diethyl S-(tert-ethylthio)methyl phosphorodithioate | 1.12 | 14.0 | 4,115 |
| Untreated Control | — | 56.0 | 16,460 |

EXAMPLE 18

Control of the Striped Seedcorn Beetle, *Agonoderus lecontei*, and Slender Seedcorn Beetle, *Clivina impressifrons* (Leconte), with O,O-Diethyl S-(tert-butylthio)methyl phosphorodithioate.

The following test was conducted with a 15% granular formulation of O,O-diethyl S-(tert-butylthio)methyl phosphorodithioate and the standard Diazinon as a treatment for the control of seedcorn beetles infesting Blue Lake snap beans in Illinois on silt loam soil. One-row plots 30 feet (9 m) long were treated in-furrow and planted on three planting dates approximately two weeks apart. Rate of treatment was 6.67 lbs. of O,O-diethyl S-(tert-butylthio)methyl phosphorodithioate 15% granular per acre (7.47 kg/ha) in 24-inch (59.3 cm) rows (1.0 lb./acre actual or 1.12 kg/ha). Evaluation was accomplished by counting the number of dead seedcorn beetles per plot about one week after treatment. Results are reported in Table XXIII below.

TABLE XXIII

Seedcorn Beetle Control

| Compound | Rate | Number of Dead Beetles | |
| --- | --- | --- | --- |
| | | Slender | Striped |
| O,O-Diethyl S-(tert-butylthio)methyl phosphorodithioate | 7.47 kg/ha | 7 | 6 |
| Diazinon (33%) | 2.5 g/kg of seed | 1 | 2 |
| Check | — | 0 | 0 |

EXAMPLE 19

Control of White Grubs, *Phyllophaga anoxia*, with O,O-Diethyl S-(tert-butylthio)methyl phosphorodithioate.

In the following tests, 15% granular formulations of O,O-diethyl S-(tert-butylthio)methyl phosphorodithioate and O,O-diethyl S-(ethylthio)methyl phosphorodithioate were evaluated for the control of white grubs infesting Irish potatoes.

The test compounds were applied at 3.0 lbs. ai/acre (3.36 ai kg/ha) in 28-inch (71.12 cm) rows. Plots on well drained loam soil, consisted of two-row treatments 60 feet (18 m) long replicated four times. Russet Burbank potatoes were treated by applying the chemicals in the furrow as bands on either side of the seed piece at planting.

Evaluations were made by determining the percentage of tubers injured by white grubs. Data obtained are reported in Table XXIV below.

TABLE XXIV

White Grub Control

| Compound | Rate kg/ha ai | Average Percent Tubers Damaged |
| --- | --- | --- |
| O,O-Diethyl S-(tert-butylthio)methyl phosphorodithioate | 3.36 | 5 |
| O,O-Diethyl S-(ethylthio)methyl phosphorodithioate | 3.36 | 10.6 |
| Control | — | 14.6 |

EXAMPLE 20

Control of Seedcorn Maggot, *Hylemya platura* with O,O-Diethyl S-(tert-butylthio)methyl phosphorodithioate.

The control of seedcorn maggots on snap beans with O,O-diethyl S-(tert-butylthio)methyl phosphorodithioate was evaluated using Tendercrop variety snap bean seeds. These were planted with a dual-cone hand seeder into 15 feet (4.5 m) rows in a treated randomized complete block design using four replicates. In-furrow application of O,O-diethyl S-(tert-butylthio)methyl phosphorodithioate 15% granular formulation was made with the hand seeder at the rate of 0.5 lb ai/acre (0.56 ai kg/ha) at planting. O,O-Diethyl S-(ethylthio)methyl phosphorodithioate 15% granular formulation was applied at 0.5 lbs. ai/acre (0.56 ai kg/ha) in a 2-inch (4.92 cm) band above the seed furrow during planting because of its known phytotoxicity when placed in direct contact with the seed. O,O-Diethyl S-(tert-butylthio)methyl phosphorodithioate was also applied above the seed furrow at the rate of 1.0 lb./acre (1.12 kg/ha) actual, as a 15% granular formulation. Rates were calculated using 36-inch (88.92 cm) row widths.

Plots were rated 3 weeks after planting by recording feeding damage to the seedlings after emergence and opening of the first leaves. Damage appeared as tunneling in the cotyledons or tattering and distortion of the first leaves. Data obtained are reported in Table XXV.

TABLE XXV
Control of Seedcorn Maggot

| Compound | Rate kg/ha ai based on 88.92 cm row | Application Method | % Seedling Damaged |
| --- | --- | --- | --- |
| O,O-Diethyl S-(tert-butylthio)methyl phosphorodithioate | 1.12 | above seed furrow | 4.7 |
| O,O-Diethyl S-(tert-butylthio)methyl phosphorodithioate | 0.56 | in flurrow | 5.8 |
| O,O-Diethyl S-(ethylthio)methyl phosphorodithioate | 0.56 | above seed furrow | 11.3 |
| Untreated Control | — | — | 30.3 |

EXAMPLE 21

Control of Cabbage Maggot, *Hylemya brassicae* with O,O-Diethyl S-(tert-butylthio)methyl phosphorodithioate.

In the following tests, O,O-diethyl S-(tert-butylthio)methyl phosphorodithioate was prepared as a 15% granular formulation and evaluated against, along with two commercial standards, the cabbage maggot. O,O-Diethyl S-(ethylthio)methyl phosphorodithioate was not used since it is phytotoxic to seeded cabbage.

Round-up variety cabbage was seeded at the rate of 15 seeds per foot of row in 24-inch (59.28 cm) rows on sandy loam soil. O,O-Diethyl S-(tert-butylthio)methyl phosphorodithioate was applied in the seed furrow at the rates of 1.0 and 0.75 lb. ai/acre (1.12 and 0.84 kg/ha). Diazinon 14% granular formulation was applied in the furrow at 1.12 kg/ha and Dyfonate, emulsifiable concentrate, was sprayed over the seed furrow at 1.12 kg/ha ai. Plots were single rows 27 feet (8.1 m) long replicated four times in randomized complete block design.

Evaluation was by counting the number of seedlings per plot six weeks after planting and examining 20 roots per treatment for the number of tunnels at harvesting. The results demonstrate vast superiority over the commercial standards applied at equivalent rates. Data are reported in Table XXVI below

TABLE XXVI
Control of Cabbage Maggots

| Compound | Rate kg/ha ai | Mean Number Seedling/Plot | Maggot Tunnels per 20 Roots |
| --- | --- | --- | --- |
| O,O-Diethyl S-(tert-butylthio)methyl phosphorodithioate | 1.12 | 168.0 | 0 |
| O,O-Diethyl S-(tert-butylthio)methyl phosphorodithioate | 0.81 | 107.5 | 0.5 |
| Diazinon 14 G | 1.12 | 85.5 | 4.3 |
| Dyfonate EC | 1.12 | 106.0 | 12.0 |
| Untreated Control | — | 85.3 | 18.0 |

I claim:

1. A method for protecting a corn crop characterized by providing it with residual pesticidal protection throughout the growing season against attack in the soil by corn rootworms by applying an insecticidally effective amount of the compound O,O-diethyl-S-(tert-butylthio)methyl phosphorodithioate to the soil in which said corn crop is grown.

2. A method according to claim 1 wherein said compound is applied with the corn seed in the seed furrow at a rate of from 0.3 to 3.0 pounds per acre.

* * * * *